United States Patent [19]
Laurent

[11] Patent Number: 5,633,383
[45] Date of Patent: May 27, 1997

[54] PROCESS FOR PRODUCING OPTICALLY PURE 1,4-DIHYDROPYRIDINES

[75] Inventor: Philippe Laurent, Oulins, France

[73] Assignee: Laboratoire L. Lafon, Maisons Alfort, France

[21] Appl. No.: 429,688

[22] Filed: Apr. 27, 1995

[30] Foreign Application Priority Data

May 5, 1994 [FR] France ................................. 94 05548

[51] Int. Cl.⁶ .............................................. C07D 211/86
[52] U.S. Cl. ............................................................ 546/321
[58] Field of Search ............................................. 546/321

[56] References Cited

FOREIGN PATENT DOCUMENTS

| 0273349 | 7/1988 | European Pat. Off. . |
| 0383320 | 8/1990 | European Pat. Off. . |
| 0591773 | 4/1994 | European Pat. Off. . |

*Primary Examiner*—Jane Fan
*Attorney, Agent, or Firm*—Jacobson, Price, Holman & Stern, PLLC

[57] ABSTRACT

The invention relates to a process which comprises the crystallization of a calcium salt of chiral (R or S) lactic acid esterified with a racemic dihydropyridine.

4 Claims, No Drawings

PROCESS FOR PRODUCING OPTICALLY PURE 1,4-DIHYDROPYRIDINES

The present invention relates to a process for producing optically pure 1,4-dihydropyridines.

It is known that the 1,4-dihydropyridines of formula

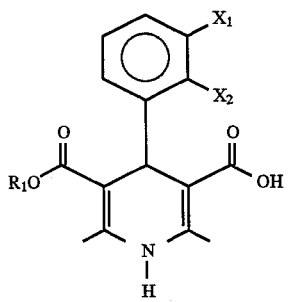

(I)

in which $R_1$ is a $C_1$–$C_4$ alkyl group and one of the groups $X_1$ and $X_2$ represents a nitro, fluoro, chloro or trifluoromethyl group and the other represents a hydrogen atom, or $X_1$ ad $X_2$ both represent a chloro group, constitute a class of compounds which are of great value for the synthesis of therapeutically useful derivatives. As examples of such derivatives, there may be mentioned nicardipine and nifedipine.

However, all these compounds have an asymmetric centre and are in the form of isomers. The ability to separate isomers or to prepare them in a form which is virtually optically pure is a critical factor.

However, no method exists at the current time for the simple and economical preparation of the dihydropyridine enantiomers of formula I.

The methods currently known are based on the separation of diastereoisomers by various routes:

use of preparative chromatography on a chiral column, which technique still cannot be industrialized, and makes use of extremely expensive stationary phases (M. Kajino etal., Chem. Pharm. Bull. 37(8) 2225–2228 (1989).

blocking of the nitrogen of the dihydropyridine with ethoxymethyl or benzyl groups, and salification of the acid function of the dihydropyridine by chiral bases of cinchonine or cinchonidine type. The salts of the two diastereoisomers thus obtained are separated by fractional crystallization. Return to the resolved acid (R or S) is done by acidification of the salt, followed by hydrolysis of the ethoxymethyl group, or by catalytic hydrogenation of the benzyl group. This process makes use of extremely expensive and particularly toxic organic bases. It must thus be certain that they have been totally removed for the subsequent operations. Moreover, the process is long and uses methods (for example hydrogenation) which, when added to the rest, can only increase the cost price of such molecules. (T. Shibanuma et al., Chem. Pharm. Bull. 28, 2809 (1980) —K. Muto et al., Arzneim. Forsch/Drug Res. 38 (II), 11a (1988).

selective enzymatic hydrolysis of the dihydropyridine carbamoylmethyl ester, this ester being difficult and expensive to gain access to. In addition, the enzymes which may be used are proteases, and especially a SEAPROSE-S, which are exorbitantly expensive (Y. Hirose et al., Tetrahedron Letters, 34, 37, 5915–5918, 1993).

The present invention is based on the observation that the calcium salts of chiral (R or S) lactic acid esterified with a racemic dihydropyridine formed two diastereoisomers whose rates of crystallization in water are extremely different. This noteworthy property has been exploited to develop a method for the resolution of dihydropyridine enantiomers having an asymmetric centre.

The subject of the present invention is thus a process for producing a 1,4-dihydropyridine of formula Ia or Ib:

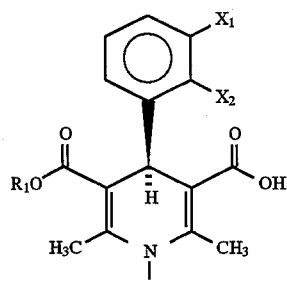

(Ia)

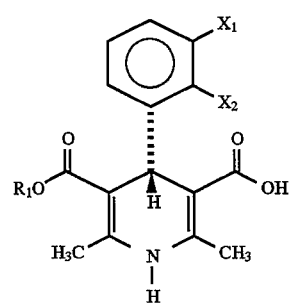

(Ib)

in which $R^1$ is a $C_1$–$C_4$ alkyl group, and one of the groups $X_1$ and $X_2$ represents a nitro, fluoro, chloro or trifluoromethyl group and the other represents a hydrogen atom, or $X_1$ and $X_2$ both represent a chloro group, which comprises the crystallization of a calcium salt of a lactic acid esterified with a racemic 1,4-dihydropyridine, of formula

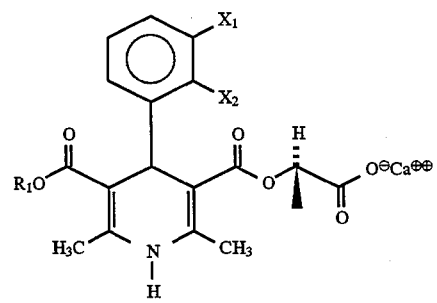

(II)

so as to separate out calcium salt crystals of formula:

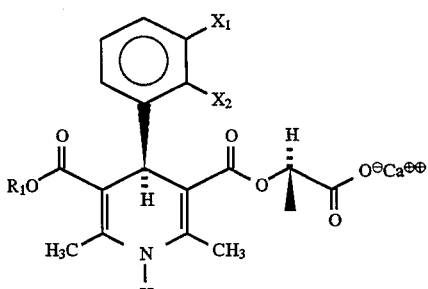

IIIa

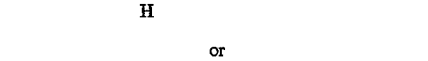

or

-continued

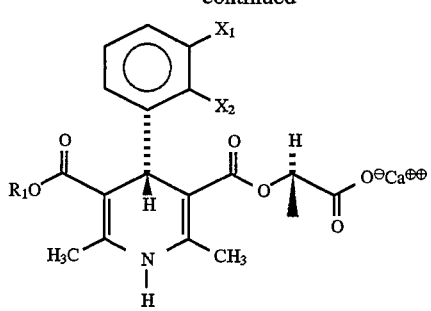
IIIb and hydrolysis of the crystallized salt IIIa or IIIb in order to obtain a 1,4-dihydropyridine of formula Ia or Ib respectively.

The preparation of the calcium salts of formula II may be performed by:

a) the reaction of an acetoacetate of alkyl (R) or (S) lactate of formula

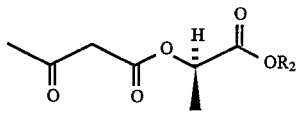
(IV)

in which $R_2$, is a $C_1$ to $C_6$ alkyl group, of an alkyl aminocrotonate of formula

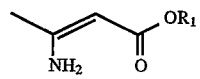
(V)

in which $R_1$ has the meaning given in claim 1, and of an aromatic aldehyde of formula:

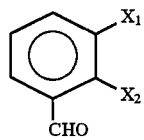
(VI)

in which $X_1$ and $X_1$ and $X_2$ have the meaning given above, in order to obtain a lactic acid ester of formula:

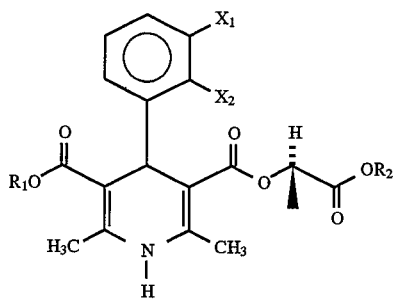
(VII)

b) saponification of the compound of formula VII under mild conditions, to obtain a compound of formula:

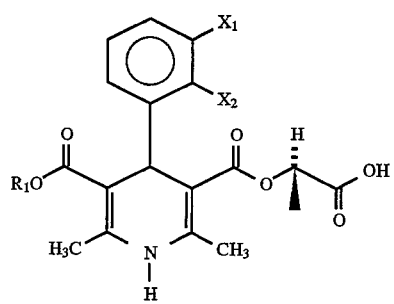
(VIII)

c) conversion of the compound of formula VIII into the calcium salt of formula II.

Thus, the dihydropyridine may be synthesized using an acetoacetate of R or S lactic ester, alkyl aminocrotonate and 3-nitrobenzaldehyde. The lactic ester is saponified in a mild manner and is then converted into the calcium salt by means, for example, of sodium hydrogen carbonate and calcium chloride. One of the two diastereoisomers crystallizes after a few minutes. It is separated out by filtration, washed and then hydrolysed in order to return to the acid. The other diastereoisomer crystallizes after several days, but it is very impure.

It suffices to choose the appropriate lactic ester in order to obtain the desired compound of formula Ia or Ib. Thus, alkyl (R)-(+)-lactate (for example isobutyl (R)-(+)-lactate) gives an (R)-(−)-dihydropyridine of formula Ia, and the alkyl (S)-(−)-lactate (for example ethyl (S)-(−) -lactate) gives the (S)-(+)-dihydropyridine acid of formula Ib.

The examples which follow illustrate the invention.

EXAMPLE 1

Preparation of (S)-(+)-2,6 -dimethyl-4-(3-nitrophenyl)-1,4-dihydropyridine-3,5-dicarboxylic acid mono-methyl ester 115 grams (1 mol) of methyl aminocrotonate and 151 grams (1 mol) of 3-nitrobenzaldehyde are added to 202 grams (1 mol) of ethyl (S)-(−)-lactate acetoacetate. The mixture is heated at between 110° and 120° C. for 4 hours. It is cooled and diluted in 1 liter of methanol. The mixture is basified, without exceeding 20° C., using 1 mol of caustic soda (d=1.33). This mixture is stirred for 10 minutes, while maintaining the temperature below 20° C.

The mixture is diluted with water, acidified and extracted with dichloromethane. The organic solution is washed with 1 liter of aqueous molar sodium hydrogen carbonate solution. The sodium salt formed above is displaced with 111 grams (1 mol) of calcium chloride dissolved in 100 ml of water, with vigorous stirring.

The calcium salt precipitates. It is filtered off and the mother liquors which preferably contain the opposite diastereoisomer are removed.

120 grams of calcium salt (0.27 mol, 54% of the expected diastereoisomer) are obtained.

After saponification in an anhydrous medium, 85 grams of crude product are isolated, which when purified give 60 grams of product (0.18 mol, 36% of the expected enantiomer).

$[\alpha]_D=+19.4(c=1.0, \text{acetone}), (\% \text{ ee})=98.0$

EXAMPLE 2

Preparation of (R)-(−)-2,6-dimethyl-4-(3-nitrophenyl-1)-1,4-dihydropyridine-3,5-dicarboxylic acid mono-methyl ester 115 grams (1 mol) of methyl aminocrotonate and 151 grams (1 mol) of 3-nitrobenzaldehyde are added to 230 grams (1 mol) of isobutyl (R)-(+)-lactate acetoacetate. The mixture is heated at between 110° C. and 120° C. for 4 hours. It is cooled and diluted in 1 liter of methanol. The mixture is basified, without exceeding 20° C., using 1 mol of caustic soda (d=1.33). It is stirred for 10 minutes, while maintaining the temperature below 20° C.

The mixture is diluted with water, acidified and extracted with dichloromethane. The organic solution is washed with 1 liter of aqueous molar sodium hydrogen carbonate solution. The sodium salt formed above is displaced by 111 grams (1 mol) of calcium chloride dissolved in 100 ml of water, with vigorous stirring.

The calcium salt precipitates. It is filtered off and the mother liquors essentially containing the opposite diastereoisomer are removed.

The crystals are washed with boiling water and then dried. 140 grams of calcium salt (0.315 mol, 63% of the expected diastereoisomer) are obtained.

After saponification in an anhydrous medium, 102 grams of crude product are isolated, which when purified give 82 grams (0.247 mol, 49.4% of the expected enantiomer).

$[\alpha]_D = -20 (c=1.0, \text{acetone}), (\% \text{ee}) = 96.8$.

I claim:

1. Process for producing a 1,4-dihydropyridine of formula Ia or Ib

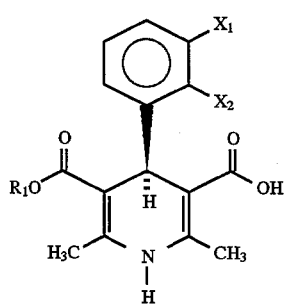

(Ia)

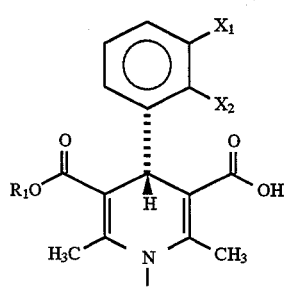

(Ib)

in which $R^1$ is a $C_1$–$C_4$ alkyl group, and one of the groups $X_1$ and $X_2$ represents a nitro, fluoro, chloro or trifluoromethyl group and the other represents a hydrogen atom, or $X_1$ and $X_2$ both represent a chloro group, which comprises the crystallization of a calcium salt of a lactic acid esterified with a racemic 1,4-dihydropyridine, of formula

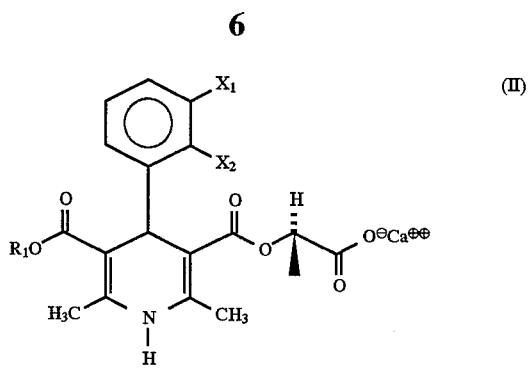

(II)

so as to separate out calcium salt crystals of formula:

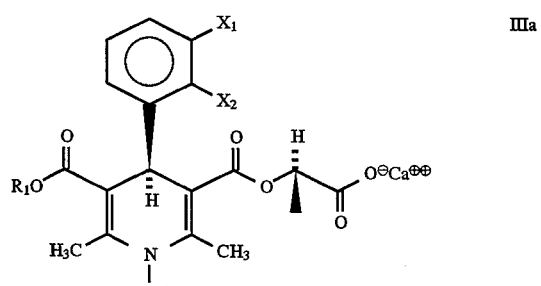

IIIa or

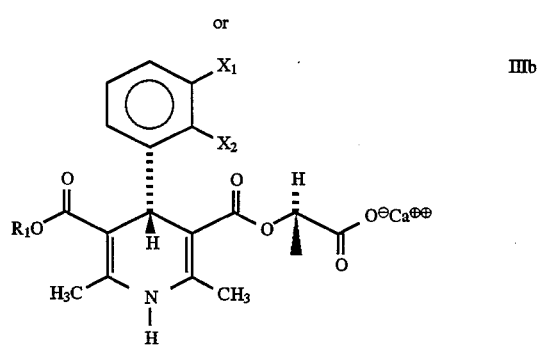

IIIb and hydrolysis of the crystallized salt IIIa or IIIb in order to obtain a 1,4-dihydropyridine of formula Ia or Ib respectively.

2. Process according to claim 1, which comprises, for the preparation of the calcium salt of formula II:

a) the reaction of an acetoacetate of alkyl (R) or (S) lactate of formula

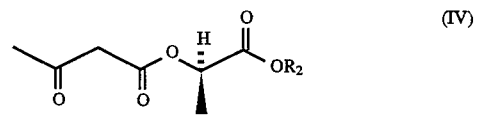

(IV)

in which $R_2$ is a $C_1$ to $C_6$ alkyl group, of an alkyl aminocrotonate of formula

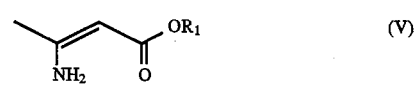

(V)

in which $R_1$ has the meaning given in claim 1, and of an aromatic aldehyde of formula:

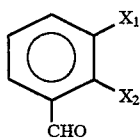

in which $X_1$ and $X_2$ have the meaning given above, in order to obtain a lactic acid ester of formula:

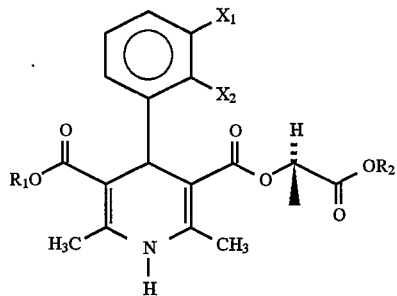

b) saponification of the compound of formula VII under mild conditions, to obtain a compound of formula:

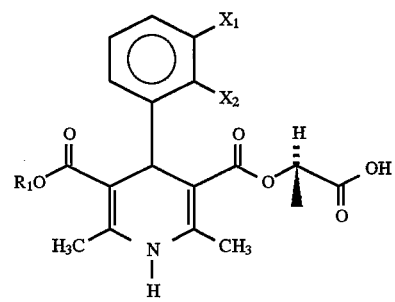

c) conversion of the compound of formula VIII into the calcium salt of formula II.

3. Process according to claim 2, in which an acetoacetate of alkyl (R)-(+)-lactate is used as compound of formula W, and an (R)-(−)-1,4-dihydropyridine of formula Ia is obtained.

4. Process according to claim 2, in which an acetoacetate of alkyl (S)-(−)-lactate is used as compound of formula IV, and an (S)-(+)-1,4-dihydropyridine of formula Ib is obtained.

\* \* \* \* \*